United States Patent
Halpern et al.

(10) Patent No.: US 10,551,450 B2
(45) Date of Patent: Feb. 4, 2020

(54) METHOD AND APPARATUS FOR RESONATOR SIGNAL PRODUCTION AND MEASUREMENT

(75) Inventors: Howard Halpern, Chicago, IL (US); Subramanian V. Sundramoorthy, Chicago, IL (US); Boris Epel, Chicago, IL (US)

(73) Assignee: THE UNIVERSITY OF CHICAGO, Chicago, IL (US)

( * ) Notice: Subject to any disclaimer, the term of this patent is extended or adjusted under 35 U.S.C. 154(b) by 1464 days.

(21) Appl. No.: 14/128,423

(22) PCT Filed: Jun. 14, 2012

(86) PCT No.: PCT/US2012/042474
§ 371 (c)(1),
(2), (4) Date: Aug. 4, 2014

(87) PCT Pub. No.: WO2012/174249
PCT Pub. Date: Dec. 20, 2012

(65) Prior Publication Data
US 2015/0022209 A1      Jan. 22, 2015

Related U.S. Application Data (60) Provisional application No. 61/496,842, filed on Jun. 14, 2011.

(51) Int. Cl.
*G01R 33/343* (2006.01)
*G01R 33/60* (2006.01)

(52) U.S. Cl.
CPC ........... *G01R 33/343* (2013.01); *G01R 33/60* (2013.01)

(58) Field of Classification Search
CPC ............................. G01R 33/60; G01R 33/343
See application file for complete search history.

(56) References Cited

U.S. PATENT DOCUMENTS 3,609,520 A * 9/1971 Sneed, Jr. ............ G01R 33/345
                                                              324/316
3,879,653 A * 4/1975 Hyde ..................... G01R 33/60
                                                              324/316

(Continued)

OTHER PUBLICATIONS

International search report from Application No. PCT/US2012/042474 dated Feb. 26, 2013.

(Continued)

*Primary Examiner* — Dixomara Vargas
(74) *Attorney, Agent, or Firm* — Marshall, Gerstein & Borun LLP (57) ABSTRACT

Techniques provide for passive Q switching in a bimodal resonator environment, where magnetic resonators are coupled for power transfer. A passive Q switch is responsive to a driving power from one magnetic resonator coupled to another magnetic resonator. After the driving power reaches a threshold, the passive Q switch shunts the receiving magnetic resonator, at least partially, to reduce the Q of that second resonator, which allows faster detection operation of the second resonator in some applications. The technique allows for fast Q switching in a bimodal resonator system, especially one having resonators having magnetic fields that are orthogonal to one another.

7 Claims, 9 Drawing Sheets

(56) References Cited

U.S. PATENT DOCUMENTS

| | | | | |
|---|---|---|---|---|
| 5,543,711 | A * | 8/1996 | Srinivasan | G01R 33/34046 324/318 |
| 5,682,098 | A * | 10/1997 | Vij | G01R 33/3415 324/318 |
| 5,739,690 | A * | 4/1998 | Rinard | G01R 33/343 324/316 |
| 6,046,586 | A * | 4/2000 | Rinard | G01R 33/343 324/300 |
| 6,137,291 | A * | 10/2000 | Szumowski | G01R 33/34084 324/318 |
| 6,150,817 | A | 11/2000 | Lurie et al. | |
| 6,198,962 | B1 * | 3/2001 | Su | G01R 33/34046 324/318 |
| 6,249,121 | B1 * | 6/2001 | Boskamp | G01R 33/34061 324/318 |
| 6,320,384 | B1 * | 11/2001 | Doty | G01R 33/34053 324/321 |
| 6,573,720 | B1 * | 6/2003 | Devasahayam | G01R 33/3415 324/316 |
| 6,693,426 | B1 * | 2/2004 | Xiang | G01N 24/10 324/300 |
| 6,806,713 | B2 * | 10/2004 | Wong | G01R 33/34053 324/307 |
| 6,946,835 | B1 * | 9/2005 | Xiang | G01N 24/00 324/300 |
| 7,030,704 | B2 * | 4/2006 | White | G04F 5/14 331/3 |
| 7,397,246 | B2 * | 7/2008 | Freytag | G01R 33/34069 324/318 |
| 7,808,241 | B2 * | 10/2010 | Dohata | G01R 33/34053 324/318 |
| 8,188,740 | B2 * | 5/2012 | Ninomiya | A61B 5/055 324/318 |
| 8,232,802 | B2 * | 7/2012 | Okamoto | G01R 33/3415 324/318 |
| 9,287,606 | B2 * | 3/2016 | Tkach | G01R 33/345 |
| 2007/0159170 | A1 * | 7/2007 | Freytag | G01R 33/34069 324/318 |
| 2008/0024133 | A1 * | 1/2008 | Vaughan | G01R 33/34046 324/318 |
| 2009/0160441 | A1 * | 6/2009 | Dohata | G01R 33/34053 324/309 |
| 2009/0302846 | A1 | 12/2009 | Wong et al. | |
| 2010/0244838 | A1 * | 9/2010 | Okamoto | G01R 33/3415 324/318 |
| 2011/0031970 | A1 * | 2/2011 | Ninomiya | A61B 5/055 324/309 |
| 2012/0235685 | A1 * | 9/2012 | Abe | G01R 33/20 324/322 |
| 2014/0218025 | A1 * | 8/2014 | Wong | G01R 33/44 324/309 |
| 2015/0185299 | A1 * | 7/2015 | Rinard | G01R 33/34046 324/322 |

OTHER PUBLICATIONS

Gor'kov et al. "Low-E Probe for $^{19}$F-$^{1}$H NMR of dilute biological solids," Journal of Magnetic Resonance 189:182-189 (2007).

* cited by examiner

METHOD AND APPARATUS FOR RESONATOR SIGNAL PRODUCTION AND MEASUREMENT

CROSS-REFERENCE TO RELATED APPLICATIONS

This application claims the benefit of U.S. application Ser. No. 61/496,842, entitled "Method and Apparatus for Resonator Signal Production and Measurement," filed on Jun. 14, 2011, the entirety of which is hereby incorporated by reference herein.

STATEMENT OF FEDERAL FUNDING

This invention was made with government support under Contract No. EB002034 awarded by the National Institute of Biomedical Imaging and Bioengineering of the U.S. Department of Health & Human Services and under Contract No. CA98575 awarded by the National Cancer Institute. The government has certain rights in the invention.

FIELD OF THE INVENTION

The present invention relates, in general, to resonators and pulse signals, particularly used in electron paramagnetic resonance (EPR) spectroscopy and EPR spectroscopic imaging.

BACKGROUND

Electron paramagnetic resonance (EPR) spectroscopy and electron spin resonance (ESR) spectroscopy are generally used to study molecular structure in chemistry, physics, biology, and medicine. EPR is also used to determine electron wave functions, lifetimes, and impurities in dielectrics used in solid state sciences. Prior EPR spectrometers comprise four main components: 1) a magnet to provide a steady DC magnetic field; 2) a high-Q microwave resonator in which a sample is placed; 3) a microwave bridge capable of producing an oscillating electromagnetic field which is coupled via a waveguide, coaxial cable, or the like to the resonator; and 4) a signal detector with field modulation, signal amplification and display systems.

In EPR, a steady magnetic field is applied to the chemical sample in the microwave resonator. The steady magnetic field causes the electrons in the sample to precess at a frequency defined by the sample composition. The precession frequency is called the paramagnetic resonant frequency and is proportional to the intensity of the applied steady magnetic field. The precession is altered by application of high frequency energy when the frequency of the energy is near the paramagnetic resonance frequency. If the sample contains unpaired electrons, the precession change can be detected. A comparison of change in electron precession as a function of magnetic field or frequency provides valuable information relating to the chemical characteristics of the sample.

The process of detection of a resonance signal involves the detection of the absorption of electromagnetic energy from a sample containing unpaired electron or nuclear spins. These spins are prepared in a magnetic field that selectively aligns the spins parallel or anti parallel relative to the preparative magnetic field; although they also respond to environmental magnetic fields. The spins couple to the magnetic fields via the magnetic moment ineluctably produced by their spins. The spins preferentially align either with or against the magnetic field producing a net magnetization of the sample, a macroscopic quantity that can absorb electromagnetic energy by which the magnetization and the spins of which it consists can be detected. This absorption takes place at a specific frequency proportional to the sum of the magnetic field produced by the preparative magnet and the environmental magnetic fields. In addition to the variation of the total magnetic field from the environment, there is a variation or spectrum of frequencies at which the absorption occurs due to lifetime broadening, an effect described by quantum mechanics. The detection of this absorption as a function of frequency can involve apparatus involving either a highly tuned system amplifying a magnetic absorption signal at a specific microwave- or radio-frequency while the preparative magnetic field is swept. The result is a spectrum of the conditions of the magnetization, which can be imaged.

Another highly sensitive method of detection is to subject the magnetization to a very short high power pulse of microwave- or radio-frequency electromagnetic energy. The short duration of the pulse means that it contains a wide band of frequencies. Ideally, this band of frequencies spans the spectrum of the magnetization. The duration of the pulse multiplied by the square root of the power of the pulse determines the angle through which the magnetization, initially oriented parallel or antiparallel to the preparative magnetic field, rotates relative to its initial direction. Having been so rotated, the magnetization precesses or rotates perpendicular to the preparative magnetic field. This precessing magnetization creates a time varying electromagnetic field of its own. This can be detected by a resonator.

A typical EPR spectrometer uses a reflection type measurement on the electrical resonator that contains the sample. In a reflection type spectrometer a single resonator is used. The sample is placed in the resonator and microwave energy is injected via a waveguide, coaxial cable, or the like into the resonator while the sample and resonator are positioned in the steady magnetic field. A microwave device called a circulator is often used to separate the desired EPR signal from the microwave source power. A disadvantage of the reflection mode of operation is that any portion of the microwave source power that is reflected from the resonator will interfere with the EPR signal generated in the resonator. In one type of measurement, also called "continuous wave" because the input microwave energy is applied as a continuous AC signal, the resonator is tuned to provide minimal reflection of the input energy when the input frequency is different from the paramagnetic resonance frequency.

The amplification provided by the resonant response of a resonator is proportional to its quality factor or Q. The Q is defined of the central tune frequency of the resonator divided by the half width at half maximum of the profile of the frequencies to which it can respond. The larger the Q and the smaller its frequency band pass, the higher the amplification and the more signal that can be detected from the precessing magnetization.

There is a problem in pulse measurements with high Q resonators. The time over which the initial, exciting pulse energy remains in the resonator is also proportional to the Q. This exciting pulse energy blinds the detection apparatus to the small magnetization signal.

Traditionally, magnetic resonance pulse experiments or magnetic resonance pulse images simply wait until the exciting pulse has dissipated in the detection apparatus before detection is begun. This is referred to as the "dead time", because it is necessary to desensitize the detection apparatus or deaden it while waiting for the excitation pulse to dissipate. However, if this dead time is too long a time interval, the magnetization itself may disappear via physical mechanisms that dissipate the coherence and the energy in the magnetization itself. There are many circumstances and substances that make detection and imaging impossible because the dead time exceeds the lifetimes of the magnetization signal.

An approach to this problem is to change the Q of the resonator very rapidly. Immediately after the exciting pulse signal, the Q is electronically spoiled or switched to a much lower value using diode switches that rapidly lowers a resistance in parallel to the resonator circuit. This shunts the excitation pulse power from the resonator to a load and much more rapidly reduces the pulse power in the resonator and shortens the time over which the detection system needs to be deadened. This in turn allows more rapid onset of detection and allows more transient signals to be detected and imaged.

Heretofore, Q spoiling has been an active process. By this we mean that external voltage signals are used to bias the diodes into states wherein they conduct current into the load resistors (lowering the Q) or block such conduction into the load resistors (increasing the Q). The external switching has its own onset time and can affect the detection system as well.

One disadvantage of reflection type spectrometers for continuous wave (CW) measurements is that the EPR signal is minute compared to the magnitude of the injected microwave energy. The signal detector must detect the EPR signal while separating out the injected microwave energy. It has proved difficult to completely separate the EPR signal from the input power.

Another difficulty arises in that any parasitic reflection of the microwave source caused by improper coupling of the input power to the resonator creates significant noise in the EPR signal. In addition, the source input waveguide and the detector waveguide must be critically coupled to the resonator to prevent a large reflection of the input power that would add to the EPR signal and saturate the detector electronics.

Phase noise or noise frequency modulation of the microwave source is converted to noise amplitude modulation in the reflected signal by the resonator, creating further noise in the EPR signal. Phase noise cannot be eliminated from microwave sources. It can be reduced but this results in higher costs. Since the phase noise intensity is proportional to the source intensity, it becomes more serious at higher powers. Hence, current EPR tools must be operated at low power which in turn requires larger samples. A phase or dispersion component of the reflected EPR signal is difficult or impossible to study in reflection-type spectrometers because of this phase noise.

EPR tools can also be used for pulse-type measurements such as electron spin echo (ESE). In pulse type measurements, the input energy is provided by a high power pulse rather than a continuous wave microwave source. The pulse causes a near instantaneous change in the precession and a gradual decay as the sample returns to the baseline state created by the DC magnetic field. In this type of measurement the difficulty in separating input power from the EPR signal requires a delay after the application of the input pulse before a measurement can be made. Because the energy stored in the resonator by the input pulse must "ring-down" or dissipate before a measurement can be taken, much of the ESE signal can be lost in a reflection-type spectrometer.

A common type of resonator used in EPR spectrometry is the cavity resonator. Cavity resonators were used in early spectrometers due to their easily modeled performance, availability, and high Q. Cavity resonators are called distributed element circuits because the microwave, magnetic, and electric field are continuously distributed and mix throughout the cavity. Characteristic dimensions of cavity resonators are of the same order of magnitude as the wavelength of the electromagnetic fields used. More recently, lumped element resonators have been suggested because their dimensions can be much smaller than the wavelengths of interest.

These conventional cavity resonators are typically ill suited for the study of lossy dielectric samples, which includes most biologicals and solutions of free radicals. The sample volumes of lossy living tissue utilized by the conventional cavity resonators are measured by the tens of microliters because high frequency microwaves suitable for resonators are absorbed in larger volumes. However, biological samples are often limited in supply which presents a particularly troublesome problem since employing a conventional cavity resonator to study transient processes usually requires large volumes of relatively concentrated material. Another problem arises from the failure of the conventional cavity resonator to effectively isolate the region of microwave electric field ($E_1$) from the region of microwave magnetic fields ($H_1$), the latter of which induces the desired EPR transitions. The inability to separate the $E_i$ and $H_1$ components is an important characteristic since the electric field may often interact with a sample to cause resonant frequency changes and Q losses (Q is the quality factor, either calculated as being 2 pi times microwave energy stored by the device/energy dissipated per cycle of microwaves or calculated as the resonant frequency ($\upsilon_0$) of the device/the difference in frequency ($\Delta\upsilon$) obtained at the 3 dB half power absorbing points on the mode pattern of the device). This undesirable interaction between the sample and the $E_1$ component is especially pronounced with lossy dielectric samples.

The Alderman-Grant resonator (AGR) is a popularly used saddle coil resonator used in water proton nuclear magnetic resonance (NMR) based MRI for localized imaging, although it can be used for whole body imaging. The resonator produces a radiofrequency or microwave magnetic field perpendicular to the axis of the cylindrical sample container. One of the attractive characteristics of the Alderman-Grant design is the excellent containment of electrical fields within the structures of the resonator, shielded from the sample in the cylindrical sample container while producing a time varying (oscillating) magnetic field to excite nuclear or electron spins in the sample. This time varying magnetic field generates magnetization in the sample. The corresponding time varying electric fields generate energy loss and shift in resonator tune that interferes with measurements. By containing the electric fields within the resonator structures, the Alderman-Grant type resonator is a very stable magnetization generator and detector.

A design more recently used for continuous and stopped flow EPR is based on a loop gap resonator (LGR) as described in Froncisz and Hyde (1982). The standard design for an LGR utilizes a machined MACOR® ceramic block having two holes extending through the block, these holes are connected by a thin slit extending through said block, the interior of the holes and slit are plated with silver. Unlike the conventional cavity resonators the LGR utilizes a much smaller sample volume; however, due to the complex configuration of the LGR and its small components the LGR based EPR probe is typically susceptible to a significant loss of sensitivity with use. In addition, due to the configuration of the loop and gap areas of the LGR low Q is experienced due to electric field ($E_1$) interaction with lossy dielectric samples. In addition, due to the design of the LGR, flow and stopped-flow induced noise is a limiting factor when utilizing stopped flow technology since repetitive starting and stopping of the sample flow in the capillary is required. This forced movement within the capillary tube creates vibrations which effectively limit the sensitivity of the LGR. In addition, the structure of the LGR makes it difficult to assemble and disassemble the device. In the event any particular part becomes contaminated or worn, the ability to replace or repair any individual component takes considerable effort and often requires returning the part to the manufacturer. In addition, the use of delicate and complex machined parts results not only in less durable parts but in expensive replacement parts. Furthermore, variable capacitance coupling used in connection with the LGR probe often causes large resonance frequency changes when the coupling is changed. The resulting simultaneous coupling and frequency changes greatly complicate attaining critical coupling One means that has been tried in order to reduce the problems associated with reflection type resonators is a bimodal resonator. The development of a practical bimodal resonator for EPR has been sought for over 20 years. A bimodal cavity resonator was commercially available from Varian Associates, Inc., but suffered from complex and difficult tuning requirements related to the cavity resonator design. Most recently, a bimodal loop gap resonator was investigated for EPR spectroscopy. In 1992 A. I. Tapin, James S. Hyde, and W. Froncisz published a paper entitled Bimodal Loop-Gap Resonator in the Journal of Magnetic Resonance 100, 484-490 that proposed a loop-gap resonator in which the two orthogonal EPR modes did not overlap in some regions of space but overlapped and were orthogonal in the sample-containing region. Unfortunately, a commercially viable implementation has not been produced. A need exists for a resonator structure for EPR spectroscopy that effectively isolates the input power from the detector yet is easy to tune and inexpensive to build.

The limitations of prior resonator structures are a primary impediment to the application of EPR spectroscopy to biology and biomedical research. Biological and biomedical applications of EPR spectroscopy are limited by low signal-to-noise resulting from the small number of spins in the sample and instrumental sources of noise, e.g., microwave source noise, magnetic field modulation, detector noise, and, in time-domain EPR, by the dead-time of the system after the microwave pulse. Because EPR is able to detect and analyze "free radicals" and metalloenzymes either naturally occurring or used as labels or probes, overcoming these impediments to EPR spectroscopy for biological samples has important commercial and scientific significance.

SUMMARY OF THE INVENTION

The present disclosure provides a technique for pulse signal production, known as passive Q-switching. Passive Q-switching involves placing the switching diodes in a configuration such that they directly sense and use the voltages produced by the excitation pulse itself to push them into the appropriate state of conduction or non-conduction. This technique avoids latencies introduced by the active switching controls. It also avoids the transient signals they introduce that can perturb the sensitive detection system. This can be used both with a simple reflection resonator or a bimodal resonator.

In another aspect of the present disclosure, a resonator structure having an Alderman-Grant resonator and a loop gap resonator that can be arranged with the same cylindrical axis for their sample holders is also described. The resonators act as a bimodal structure with one exciting the magnetization and the other detecting the produced magnetization. Because the magnetic fields produced or detected by each structure are perpendicular, one structure is isolated or desensitized to the magnetic field produced by the other. To the extent of this isolation, large pulses of power may be delivered to the spins in a living sample by one resonator with minimal detection in the other resonator.

In accordance with an example, a method for modulating the quality factor (Q) of a resonator comprises: reducing the Q, from a high value, during an excitation time; and returning the Q to the high value during a detection time.

In accordance with another example, a bimodal resonator apparatus comprises: a first magnetic field resonator; and a second magnetic field resonator, wherein the bodies of the first magnetic field resonator and the second magnetic field resonator are positioned concentrically, and the magnetic field created by the first magnetic field resonator is orthogonal to the magnetic field created by the second magnetic field resonator.

BRIEF DESCRIPTION OF THE DRAWINGS

FIG. 5 illustrates the AGR/LGR resonator externalized from its mechanical support and matching circuitry. The shunting resistor of the loop gap resonator is removed; and the Alderman-Grant resonator mechanical support is removed. The Alderman-Grant resonator has a slot on the top to allow connections to loop gap resonator and space for frequency defining capacitor. The Alderman-grant resonator feeds are visible at the bottom. The Alderman-Grant resonator in the final assembly is attached to the RF shield while the Loop Gap resonator is attached inside the Alderman-Grant resonator, placed so that its cylindrical axis is coincident with that of the Alderman Grant resonator but its $B_1$ is perpendicular to that of the LGR to produce orthogonal to $B_1^{LGR}$ and $B_1^{AGR}$. This creates a physical decouping of the field of the excitation resonator from that of the detection resonator.

DETAILED DESCRIPTION

The present disclosure provides a technique for pulse signal production, known as passive Q-switching, in either single mode resonator or bimodal resonator configurations. In some examples discussed herein, a highly decoupled bimodal resonator is provided, formed of an Alderman-Grant/Loop Gap resonator system, where the Alderman-Grant resonator acts as a first, excitation resonator, and the loop gap resonator acts as a second, detection resonator. For a bimodal resonator, with the isolation decoupling a detection resonance from an excitation resonance, e.g., decoupling power of approximately 40 dB in the discussed example, reducing an instantaneous excitation power of 60 dBm to 20 dBm for detection power, a passive Q switch may be used as a protection switch for the output of the detection resonator into the sensitive and easily saturated low noise amplifier, often the first element in the detection system. For a single modal resonator, passive Q switching may be used to selectively reduce the Q of the resonator, if the Q value is too high for a given application, where the Q switching occurs in response to a high drive power input signal to the single modal resonator. The lower Q enables much more rapid ring down of the excitation power, allowing detection much earlier in the decay of the excited magnetization.

Figure 1:
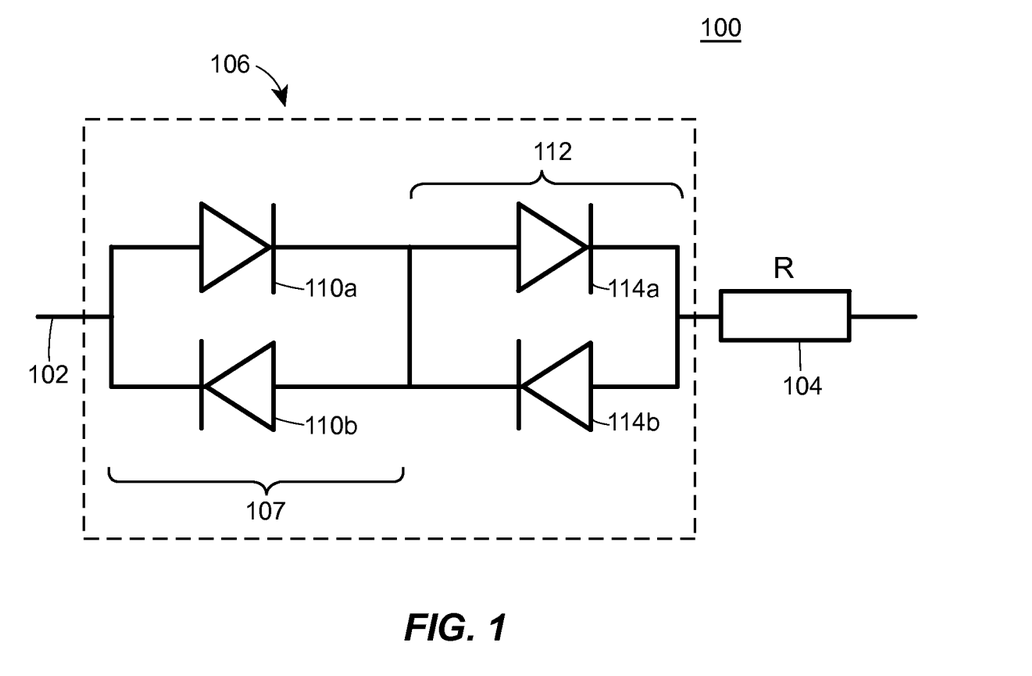
FIG. 1 illustrates an electronic diagrammatic scheme of a passive Q modulator.
Figure 2:
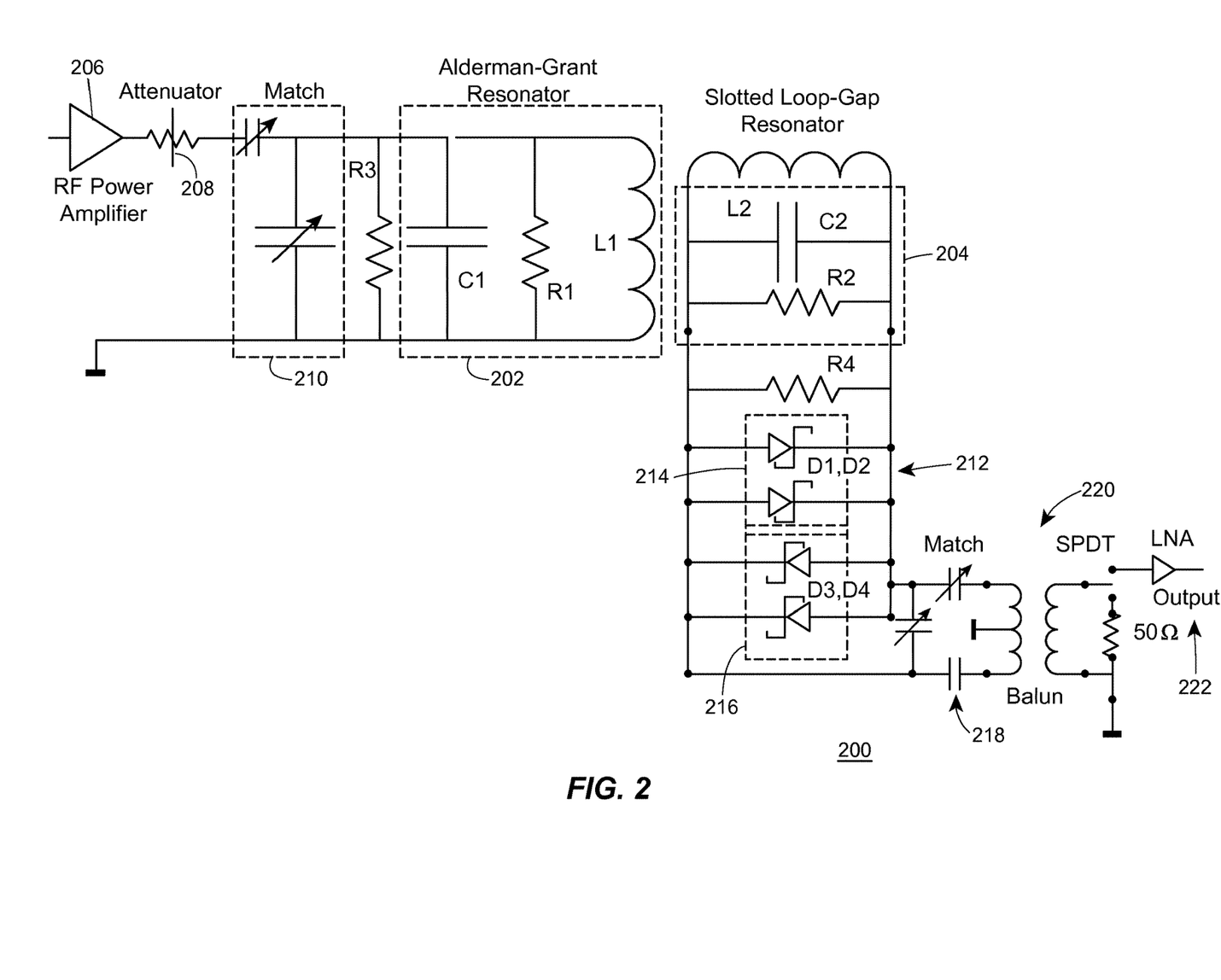
FIG. 2 illustrates the circuit diagram for an Alderman-Grant resonator (AGR) and a slotted loop gap resonator (LGR) forming a bimodal resonator with balanced couplings (baluns) to coaxial input and output cables.

As discussed further, passive Q-switching in some examples involves placing switching diodes in a configuration such that they directly sense and use voltages produced by an excitation pulse itself to push them into the appropriate state of conduction or non-conduction (FIG. 1 and FIG. 2). This technique avoids latencies introduced by active switching (Q switching) controls. It also avoids the transient signals they introduce that can perturb the sensitive detection system.

FIG. 1 illustrates a schematic model 100 of a passive Q modulator or switch as may be used with a bimodal resonator or with a single modal resonator. The model 100 has a signal input 102, a load 104, which may represent a coaxial output cable having a resistor R, and a passive Q switch stage 106, formed of a first portion 107 having a first Shottky diode pairing 110a and 110b and a second portion 112 having a second Shottky diode pairing 114a and 114b.

FIG. 2 illustrates an example implementation of a passive Q switch, like that of FIG. 1, implemented in a bimodal resonator 200 formed of a first magnetic field resonator 202, which is an Alderman-Grant resonator (AGR) in the illustrated example, and a second orthogonally coupled magnetic field resonator 204, which is a slotted loop gap resonator (LGR) in the illustrated example. The AGR operates as an excitation resonator and the LGR operates as a detection resonator. While examples herein are described in reference to particular types of orthogonally coupled resonators, and having the ability reduce and increase Q factor at different times, it will be appreciated that the present application is not limited to a particular type of resonator or combination of resonators. For example, in other examples, the LGR is the excitation resonator and the AGR is a detection resonator.

The AGR 202 is coupled to an input RF signal, provided by an input RF power amplifier 206 and selectable attenuator 208, through a filtering and impedance matching stage 210 and resistor R3. The AGR 202 is inductively coupled to the LGR 204 and, as illustrated, produces a magnetic field in a first direction, while the coupled LGR 204 produces a resulting magnetic field in a second orthogonal direction.

To provide passive Q switching for the bimodal resonator 200, a passive Q modulator 212, also termed a "passive Q switch" herein, is provided, similar to that of the passive Q modulator of FIG. 1 and formed of a first pairing of Schottky diodes 214 and a second pairing of Schottky diodes 216. In the illustrated example, the passive Q switch 212 is coupled to the detection resonator, LGR 204, and more specifically is coupled between the resonator 204 and an impedance matching output stage 218 and a balun 220 providing a balanced/unbalanced transform to a coaxial cable coupling stage 222.

Different from an active switch, which is controlled by external voltage level, the passive Q switch 212 is activated by the applied power itself. In the case of a bimodal system, that applied power is the power coupled from the excitation resonator 202 to the detection resonator 204. In the case of a single modal system, that applied power would be the power supplied to the single resonator. Because the passive Q-switch 212 is activated by the level of applied power, e.g., coupled from the AGR 202 to the LGR 204, the action of the Q switch is limited to power decays from the applied power to −5 to 2 dBm, for example. The particular Q switch operating range is not limited to this applied power range, but rather may be set to any desired range, depending on the turn on conditions set by the schematic configuration of the Q switch.

The bimodal resonator may be used as part of an EPR or ESR spectroscopy system. Pulse EPR or ESR images require systems with much larger frequency response and hence lower Q than conventional spectroscopic systems. Samples are imaged using fixed stepped gradients added to the preparative magnetic field. This encodes location of sample planes in the net magnetic field which are constant in planes within the sample but which vary in the direction perpendicular to the net gradient direction which can be rotated. The varied magnetic field corresponds to varying resonant frequencies so that the image location is said to be frequency encoded. To encompass the entire sample a large range of frequencies must be responded to. At relatively high imaging Q of approximately 30 the performance of passive Q-switch is comparable with performance of active Q-switch. In principle, the externally controlled active switch should further reduce the dead time by extending protection interval to lower powers. However, since the transient signals generated by active switch may be comparable with signals of ringing resonator, the real advantages of active Q-switching are considerably smaller.

Figure 3A:
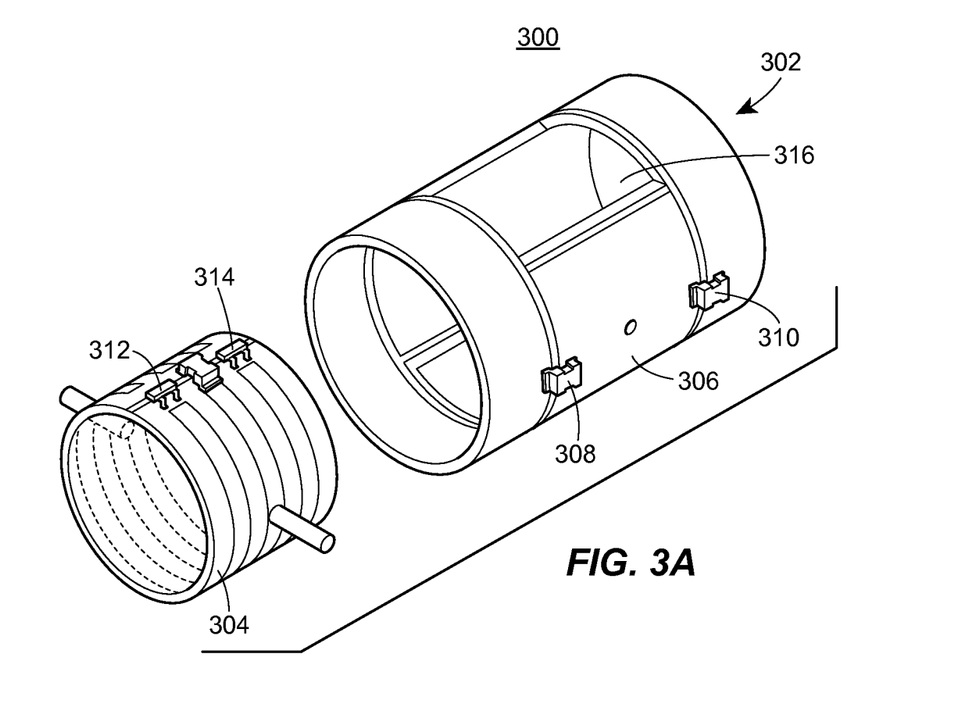
FIG. 3A is a perspective view of the Alderman-Grant resonator and slotted loop gap resonator of FIG. 2, unassembled and forming a bimodal resonator. The bimodal resonator operates with a passive Q spoiling function achieved using Schottky diodes (e.g., HSMS-2805 1 Amp, 70V reverse break down voltage diodes) connected in an anti-parallel configuration. Diodes D1 and D2 are in one chip; and diodes D3 and D4 are in another chip, where the two are surface mountable. Chips are soldered directly on the 4 turn slotted loop gap resonator in the receiver arm of the bimodal resonator. The transformer coupled balun is TP-101-PIN from M/A come Technology Solutions
Figure 3B:
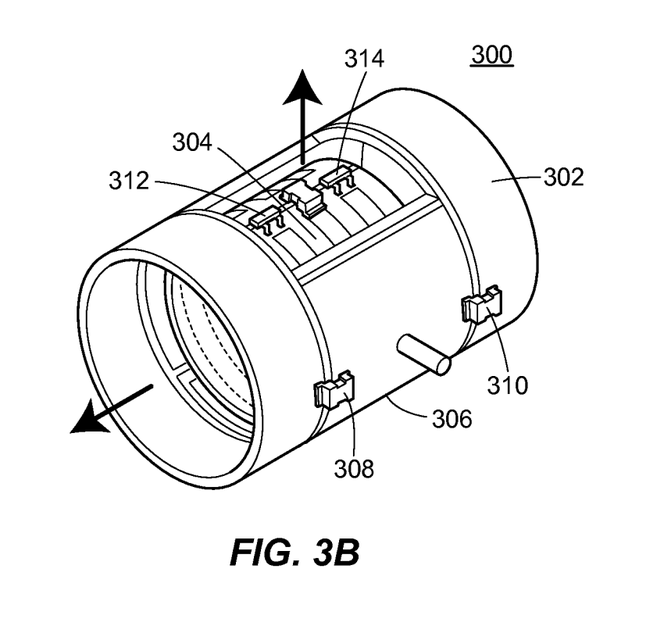
FIG. 3B is a perspective view of the bimodal resonator in an assembled form.

In the illustrated example, the passive Q switch 212 is based on the Schottky diode pairs 214 and 216 connected in parallel to a capacitor (C2) of the loop gap resonator 204. An example bimodal resonator 300 with integrated passive Q switch is shown in FIG. 3A and FIG. 3B. The resonator 300 includes an AGR 302 with an embedded LGR 304 in a concentric configuration, in the illustrated example. The AGR 302 is formed of an outer resonator structure 306 with two integrated Schottky diodes 308 and 310. The LGR 304 is positioned within an inner chamber of the resonator structure 306 and has a slotted configuration, with two Schottky diodes 312 and 314. The diode pairs 308/310 and 312/314 are electrically coupled in parallel as illustrated in either FIG. 2 or FIG. 3. In the illustrated example, the diodes 312/314 are positioned on platform of the slotted LGR 304 coinciding with a spacing gap 316 in the resonator structure 306. It is noted that in other examples, the AGR resonator may be concentrically disposed within an LGR resonator.

In operation, the bimodal resonator 300 maintains Q of the resonators AGR 302 and LGR 304, in a first operating range, then decreases the Q of the resonators AGR 302 and LGR 304 is a second operation range, in a second operating range. For example, at power levels below −5 dBm, the diodes are not conducting and do not affect the Q of the resonator. At higher power levels the diodes 308, 310, 312, and 314 turn on and conduct current thereby shortcutting the resonator. This reduces Q. At approximately 2 dBm all applied power falls on the diodes 308, 310, 312, and 314; and voltage on the diodes 308, 310, 312, and 314 is power independent. This way passive Q-switching not only reduces the Q and resonator dead time but protects downstream circuitry from power damage. As the diodes shunt the LGR resonator in response to excitation, the drive to the diodes diminishes until the diodes turn off, which then begins to return the Q of the resonator to its value pre-shunting by the passive Q switch, where depending on the duty cycle of the excitation pulses from the AGR resonator, the Q may return to its full pre-shunting value.

In the illustrated example of FIG. 2, the Q-switch is connected across the inductive loop/gap of the LGR. The LGR is critically coupled during application of high power (e.g., 17 dB). The Q of the LGR during high power is denoted $Q^H_{CC}$. During application of low power (e.g., −15 dB) the Q of the LGR is increasing but the LGR becomes overcoupled and the effective Q is then $Q^L_{OC}$. By recoupling of the LGR, the critically coupled $Q^L_{CC}$ at low power can be measured. Note that resonance frequency of the LGR in this case is shifted up.

In principle, the operational mode of Q-switch can be different. The LGR can be critically coupled at low power. This mode of operation provides a slightly higher signal; however since high power causes undercoupling of the resonator, this mode is not very efficient, especially for bandwidth. In principle, another resistor parallel to the given circuit can be installed to decrease the difference between $Q^H_{CC}$ and $Q^L_{OC}$. For the diodes with rather high capacitance used in the current design, this resistor is not necessary.

The application of the above passive Q-switching applies to any resonator system applied to the measurement of any system responding to a short high power energy pulse. It is particularly valuable for electron paramagnetic resonance (EPR) signal detection and EPR imaging because of the relaxation times, the times over which transient magnetizations diminish by 1/e (=½.718=0.368) times its initial value. However, it would be applicable to NMR measurements in the solid state where relaxation times are quite short and NMR is used for mining exploration.

Two application modes were tested: i) mode 1—high bandwidth for OX63H and ii) mode 2—low bandwidth for OX63D. For comparison standard dumping resistor is installed across the inductor/loop.

Mode 1:

| R [kΩ] | BW [MHz] | $Q^H_{CC}$ | $Q^L_{OC}$ | SNR |
|---|---|---|---|---|
| | | Q-switch | | |
| 500 | 9.1 | 11 | 21 | 1.33 |
| | | Reference | | |
| 750 | 9 | 13.5 | 13.5 | 1 |

$Q^L_{CC}$ is 30. Pulses 35 ns. Power for Q-switch design 60-7 dBm. Protection switch 340 ns. Dead time 550 ns.

Mode 2:

| R [kΩ] | BW [MHz] | $Q^H_{CC}$ | $Q^L_{OC}$ | SNR |
|---|---|---|---|---|
| | | Q-switch | | |
| 1.495 | 4.8 | 23 | 39 | 1.29 |
| | | Reference | | |
| 1.8 | 4.8 | 30 | 30 | 1 |

$Q^L_{CC}$ is 47. Pulses 65 ns. Power for Q-switch design 60-15 dBm. Protection switch 440 ns. Dead time 650 ns.

Figure 4A:
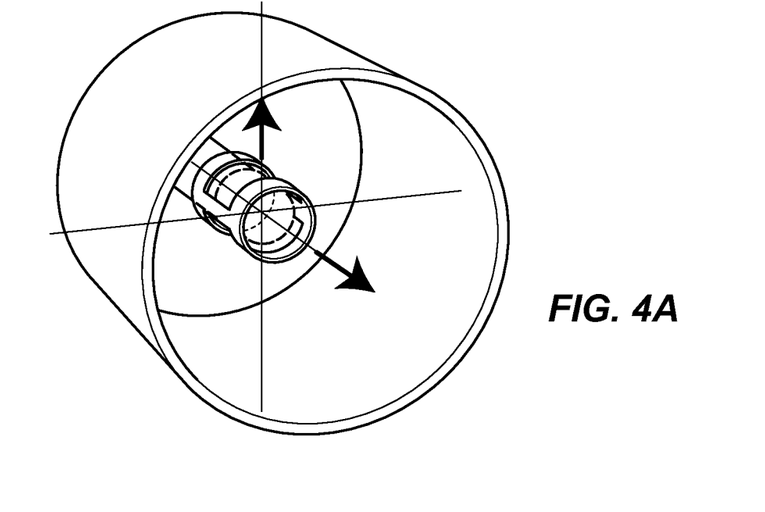
FIG. 4A illustrates a layout of the RF coils of the bimodal resonator, showing inner coils of the loop gap resonator and rendition of the outer coil of the Alderman-Grant resonator (end-ring coils are not shown). Arrows show the orthogonal nature of the magnetic fields produced by each resonator: $B_1^{LGR}$ (along shield axis) and $B_1^{AGR}$ (up) directions in the geometrical center of resonators. B.
Figure 4B:
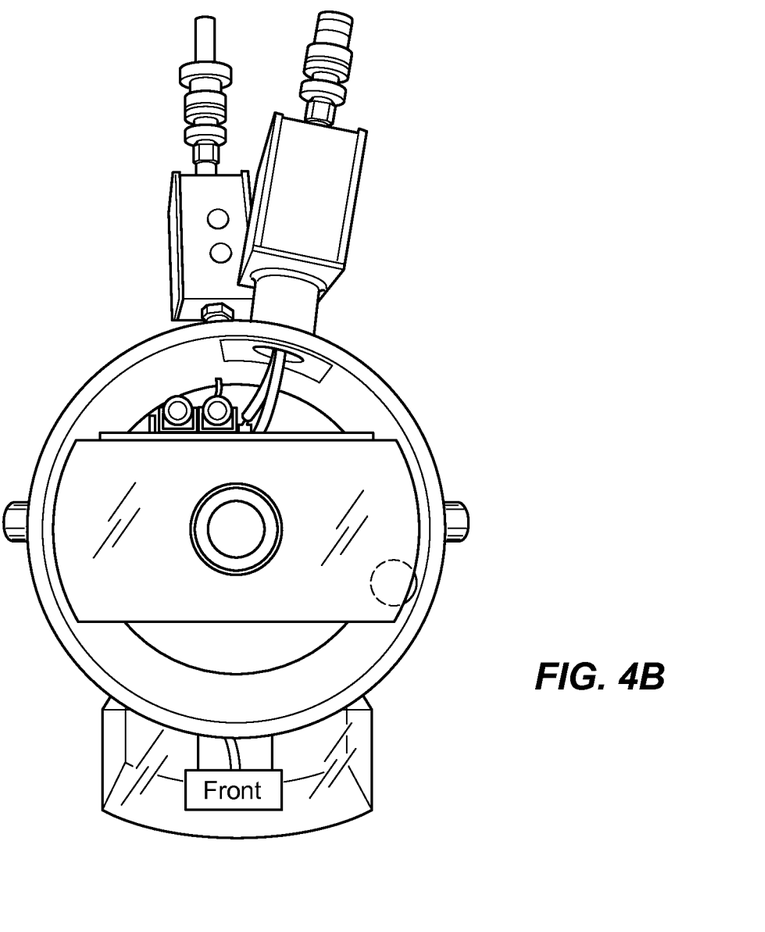
FIG. 4B illustrates an assembled bimodal resonator.
Figure 5:
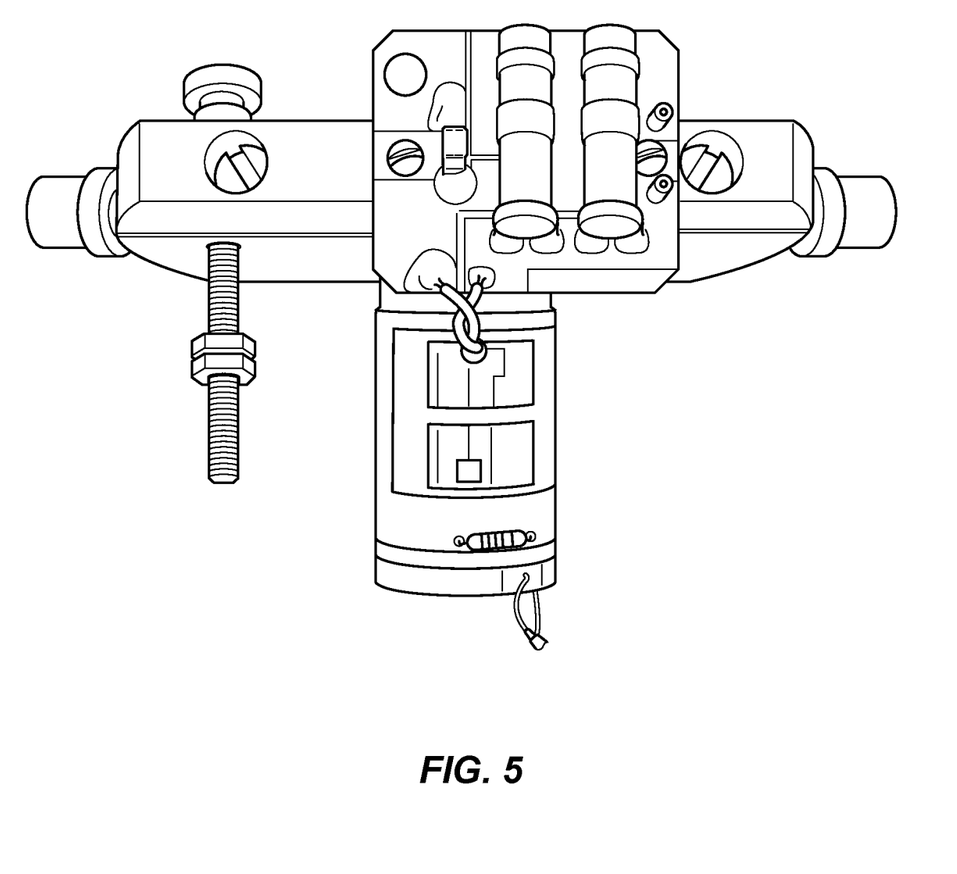

The present disclosure also provides for a resonator structure. As discussed above, the resonator structure may include an Alderman-Grant resonator and a loop gap resonator that can be arranged with the same cylindrical axis for their sample holders (FIG. 4A and FIG. 4B). The resonators act as a bimodal structure with one exciting the magnetization and the other detecting the produced magnetization. Because the magnetic fields produced or detected by each structure are perpendicular (FIG. 5), one structure is isolated or desensitized to the magnetic field produced by the other. To the extent of this isolation, large pulses of power may be delivered to the spins in a living sample by one resonator with minimal detection in the other resonator. If the RF energy is delivered in a very short burst after which the energy rapidly dissipates, this allows the second resonator to begin detection much sooner than if it were not isolated from the first. The combination of these two specific resonator structures is unusually stable and nearly totally free from living sample motion effects on tuning and phase.

Figure 6:
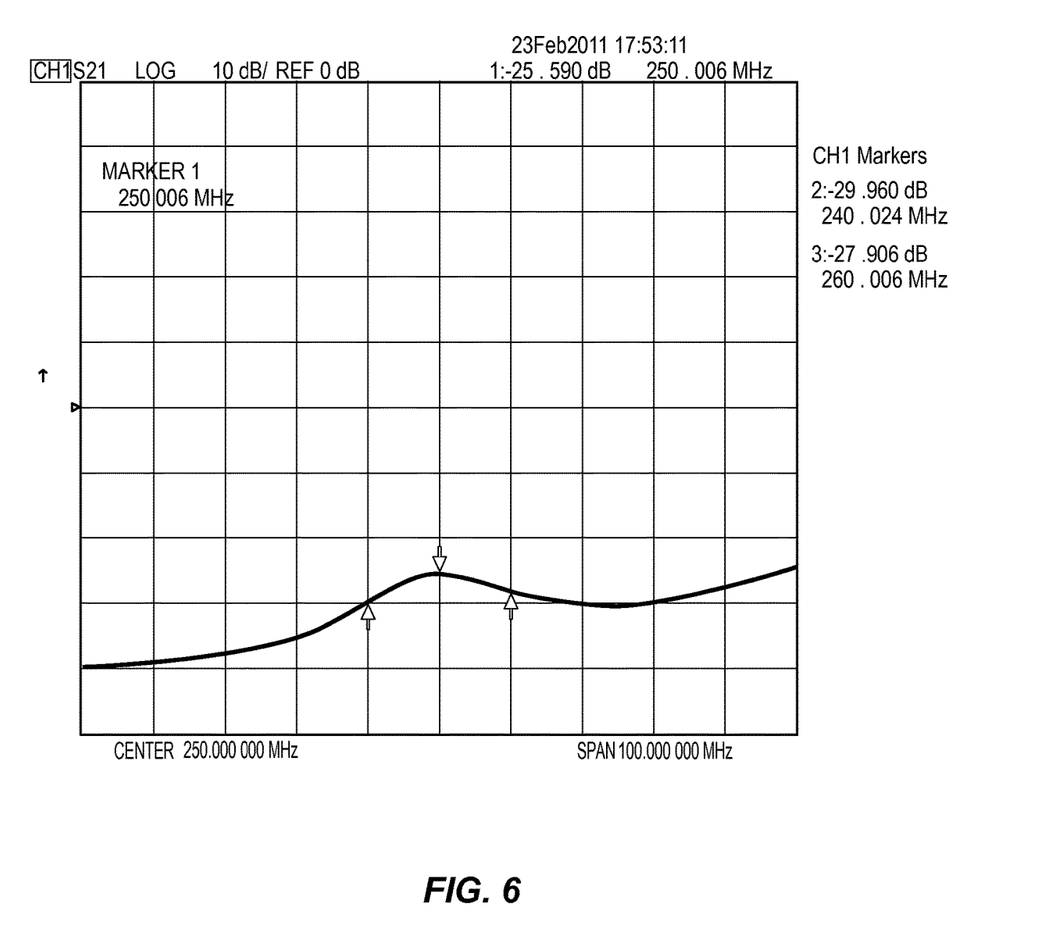
FIG. 6 is a plot of signal isolation, which was observed in all tests as better than 23 dB.
Figure 7A:
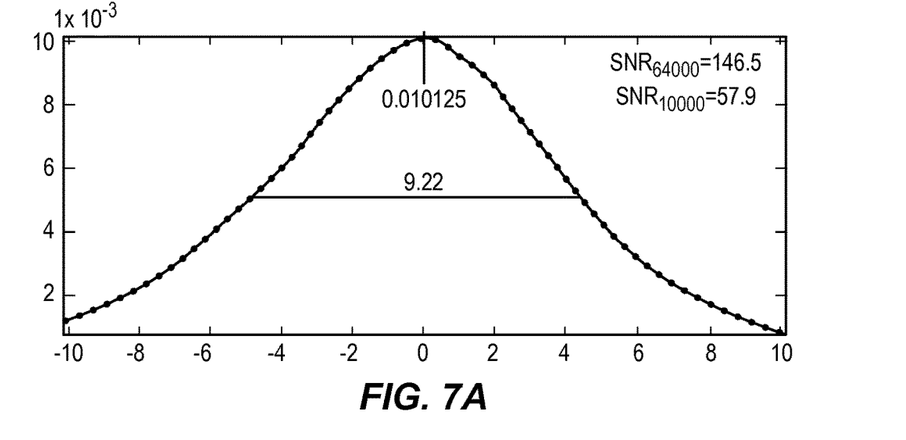
FIG. 7A is a plot of the cavity profile for a standard loop gap resonator; 19 mm loop gap resonator, air-gap capacitor coupling ESE, Pulse length 35 ns, Q=13.9.
Figure 7B:
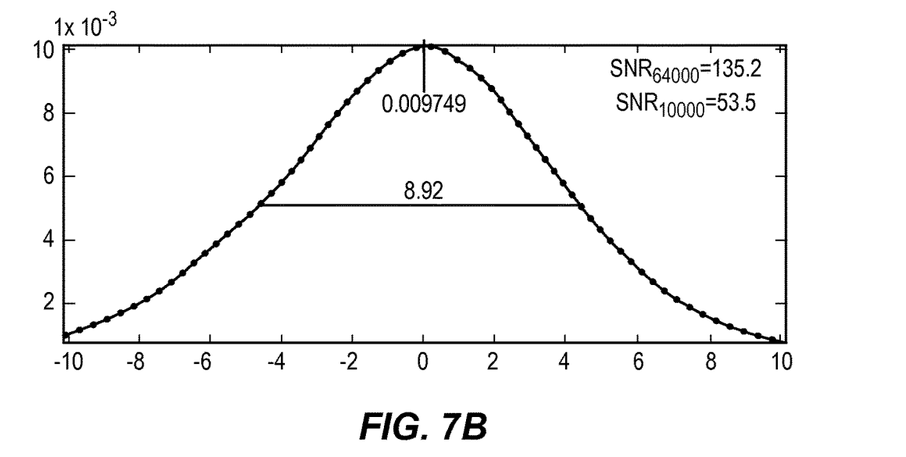
FIG. 7B is a plot of the cavity profile for standard loop gap resonator with the coupling similar to the one used for bimodal resonator; 19 mm loop gap resonator, Johanson capacitor coupling ESE, Pulse length 35 ns, Q=13.9.
Figure 7C:
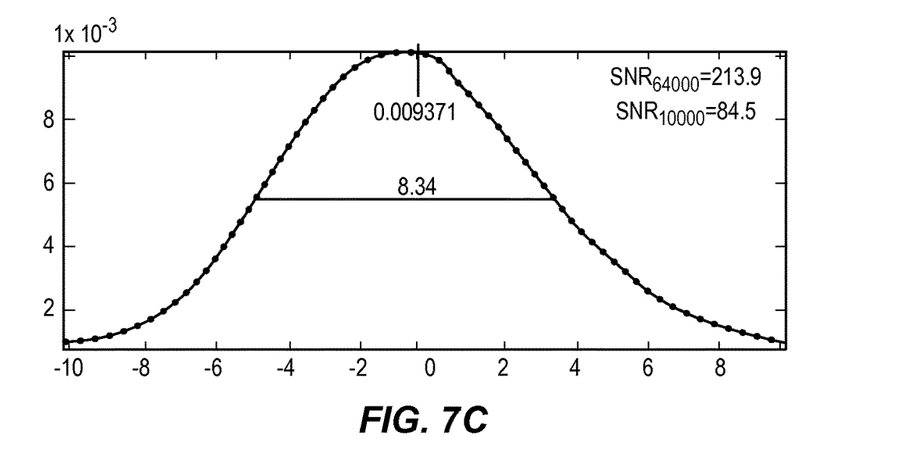
FIG. 7C is a plot of the cavity profile of the loop gape resonator of a bimodal resonator; 16 mm loop gap resonator, Johanson capacitor coupling ESE, Pulse length 65 ns, Q=10.9.
Figure 8A:
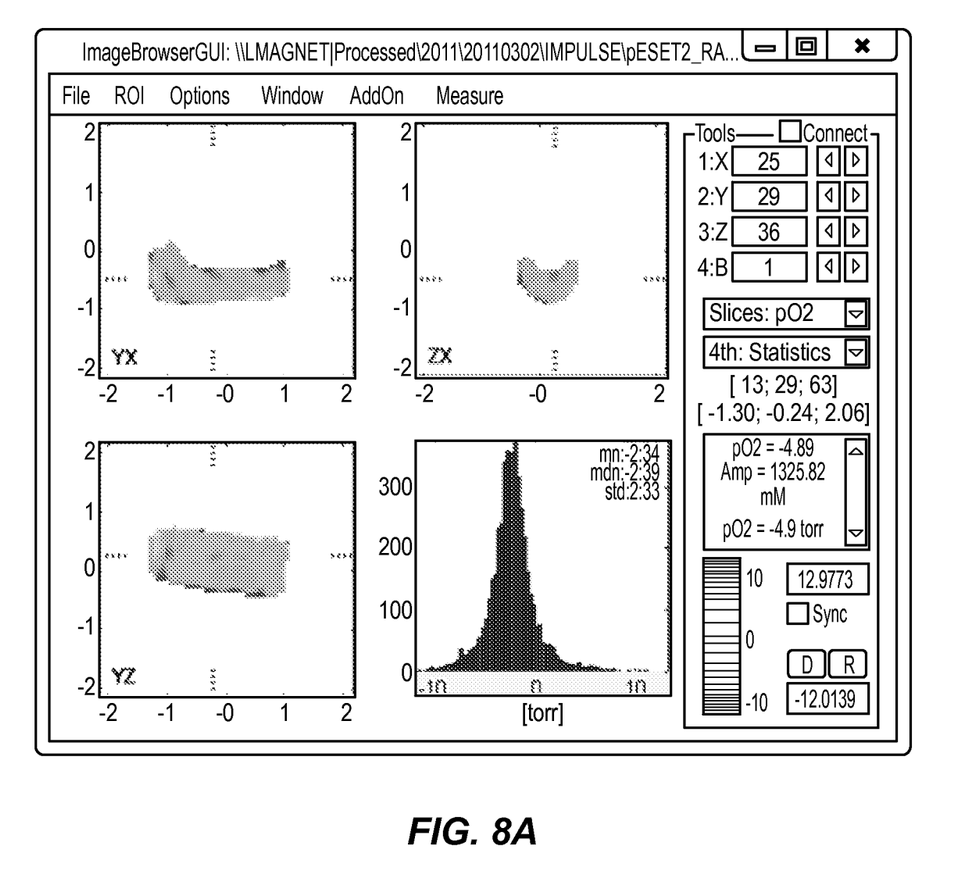
FIG. 8A illustrates a pO2 image of a deoxygenate bottle of trityl spin probe as well as the distribution of the oxygen level (pO2s) from each voxel using a bimodal resonator.
Figure 8B:
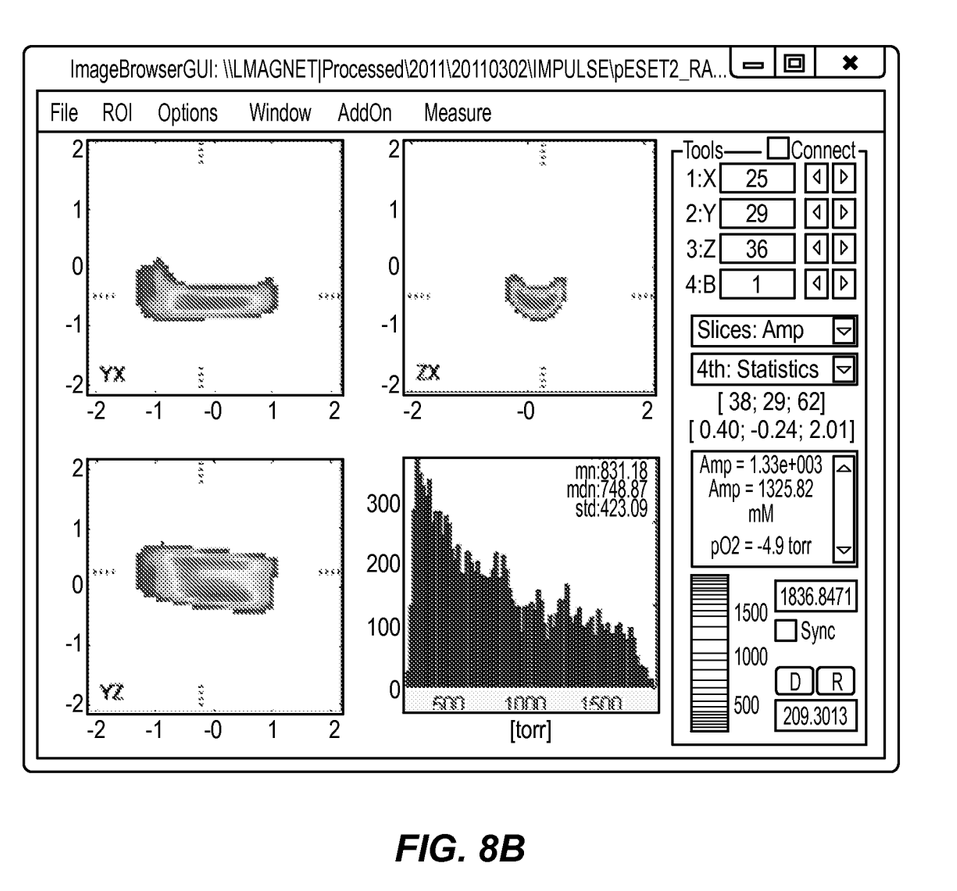
FIG. 8B illustrates distribution of the spin probe intensities from the voxels of the image from the bottle.

FIG. 6 illustrates a screen of the isolation of the AGR from the LGR as a function of frequency obtained from our network analyzer an Agilent Model 8753ES, available from Agilent Technologies, Santa Clara, Calif. This was a partial investigation of isolation due to geometric limitations in our ability to orient the AGR relative to the LGR to cancel stray, mutually sensed B1, the magnetic component of their electromagnetic radiofrequency fields. Subsequent models of the bimodal resonator have given greater than 30 dB isolation and 40 dB should be routinely possible with increased geometric reorientation capability. FIGS. 7A-C show the frequency response of a standard LGR in our lab, the specific LGR used in this bimodal at an identical Q, and that of the bimodal resonator in accordance with examples described herein. At identical Q, the frequency response of the LGR resonators are hard to distinguish. The Q was diminished for the bimodal resonator to produce the same frequency profile. FIG. 8 as indicated is the image produced from our EPR oxygen imager. The sample is a bottle of a paramagnetic molecule referred to as trityl OX063.

This species of spin probe reports the local solution oxygen pO2 through its phase memory or transverse relaxation rate. The transverse relaxation rate R2 is directly proportional to the local oxygen tension. By imposing gradients as described in the text, an image of the sample can be obtained; and the pO2 from each of the voxels or sub volumes of the image can be obtained. The distribution of the pO2 values from the bottle are shown in FIG. 8A. The trityl intensities are shown in FIG. 8B. One can see that because of edge blurring, this intensity distribution, expected to be narrow is highly blurred. The pO2 values, however are much better clustered since they are much less sensitive to the image artifact than the intensity values.

The table below summarizes the characteristics of the AGR/LGR system in an example implementation. In this configuration the excitation resonator of the bimodal resonator was the AGR. This was tuned to 250 MHz, Q=10.9, 60 dB coupling, additional mode is observed at 279 MHz. AGR was tuned at 250.0 MHz, Q=10.1, 60 dB coupling, additional mode is observed at 330 MHZ. AGR has maximum flipping angle at 54 dB of power with 65 ns pi pulse −0.05258 G/sqrt(W*Q).

|  | Method | $B_1$ [G] | V [cm$^3$] | Q | Power [W] | α [G/√W/√Q] |
|---|---|---|---|---|---|---|
| Loop gap LGR19 | Pulse, ESE, maximum signal | 5.1 | 4.25 | 14 | 125.9 | 0.12 |
| AGR (excitation) | Pulse, ESE, maximum signal | 2.7 | ~8 (not sure) | 10.1 | 250 | 0.055 |

In addition to controlling operation of the bimodal resonator through the diode turn-on voltage ratings and general circuit configuration, the operation of the bimodal resonator may be determined by the size of the inductive elements forming the AGR and LGR. For example, a bimodal resonator with a 16 mm diameter inductive element forming the LGR can be operated in the range of frequencies from very low up to about 1 GHz. The current path length along the resonator structure should typically be less than $\lambda/8$, where $\lambda$ is the wavelength in free space corresponding to the operational frequency: $\lambda=c/f$ (see, Leifer, M. C. (1997). "Resonant Modes of the Birdcage Coil." Journal of Magnetic Resonance 124: 51-60), where c is the speed of light constant. For 1 GHz, the wavelength is 30 cm and circumference of the largest resonator dimension is expected to be on the order of 4 cm.

Frequency adjustment of the resonators can be achieved by varying the capacitances or the inductances where the resonant frequency v for a system having an isolated inductance and capacitance in parallel is $v=1/2\pi\sqrt{(LC)}$. In the case of an LGR, varying the capacitances may be the simplest, although any frequency adjustment technique may be used. For the given inductance of the resonators the required capacitance is inversely proportional to the second power of the frequency, e.g., to upscale resonator from 250 MHz to 1 GHz a factor of 16 reduction of capacitance is required.

The resonator is a self-sufficient module and can be connected via a cable that can transmit radiofrequency or microwave frequency electromagnetic signals to any imager or spectrometer that allows replaceable resonators such as coaxial, twisted pair, or triaxial cables. In terms of resonator geometry, the proposed resonator has very low space requirements. The diameter of AGR resonator may be only a few millimeters larger than the diameter of active volume. This will enable use of the present resonators in commercial spectrometers/imagers. Placement of the bimodal resonator, typically will involve centering it at the geometric origin of the gradient coil system that is part of most magnetic resonance imaging magnet systems (the point at which the magnetic fields from the magnetic field gradient system is equal to 0 Tesla).

As noted above the present techniques provide for passive scaling of Q in a bimodal or single modal resonator as a function of drive power. This allows for reducing Q during an excitation time, which is the time during which the high power radiofrequency (drive power) is applied. In some examples, the excitation time may further include the time between pulses. However, operationally, in a multipulse sequence, for example a spin echo sequence where a 90° pulse rotates the magnetization into the transverse plane and is allowed to precess until a 180° pulse is applied with a phase shift to reverse the precession direction of the magnetization, the beginning of the 90° pulse to the end of the 180° pulse can be considered the excitation time. In active Q switching, one can control the time over which the Q is spoiled, for example extending the time beyond the actual excitation time to the time at which the greatest radiofrequency pulse power is below that which saturates the low noise amplifier. For passive Q switching, the power threshold is determined (as discussed) by that point at which the diode bias reverses, which in turn defines the time over which the Q is spoiled.

In some examples, the Q discussed herein may be increased, e.g., by directing the current to a path with a higher shunt resistance or lower series resistance over a detection time, coinciding with detection in the second, LGR, resonator. The detection time may be the time over which the signal is routed to the low noise amplifier, and generally would exclude the dead time, which is the time during which the detection system is desensitized, or "deadened" to incoming signal.

In any event, with the present techniques a reduction Q is passively achieved through operating at a maximum (or threshold) power that is may be substantially larger than that necessary to begin the reversing the bias on the spoiling diode system, ~16 dBm or about 40 milliwatts into 50 Ohms. For example, pulses commonly at 50 to 60 dBm (100 to 1000 watts peak power) were sufficient. Such large power levels may be achieved in a passive system as described, whereas an active system may not be able to withstand such higher powers without higher capacitance and resulting much slower response.

While the present invention has been described with reference to specific examples, which are intended to be illustrative only and not to be limiting of the invention, it will be apparent to those of ordinary skill in the art that changes, additions and/or deletions may be made to the disclosed embodiments without departing from the spirit and scope of the invention.

Thus, although certain apparatus constructed in accordance with the teachings of the invention have been described herein, the scope of coverage of this patent is not limited thereto. On the contrary, this patent covers all embodiments of the teachings of the invention fairly falling within the scope of the appended claims either literally or under the doctrine of equivalents.

What is claimed is:

1. A bimodal resonator apparatus comprising:
   a first magnetic field resonator;

a second magnetic field resonator,
wherein
the bodies of the first magnetic field resonator and the second magnetic field resonator are positioned concentrically, wherein the first magnetic field resonator is positioned within the second magnetic field resonator,
the magnetic field created by the first magnetic field resonator is orthogonal to the magnetic field created by the second magnetic field resonator, and wherein the first magnetic field resonator and the second magnetic field resonator have the same resonant frequency, and
the first magnetic field resonator and the second magnetic field resonator are positioned such that the magnetic field created by the first magnetic field resonator drives the magnetic field created by the second magnetic field resonator;
the bimodal resonator apparatus further comprising a passive Q switch coupled to the second magnetic field resonator and configured to affect a Q of the second magnetic field resonator in response to driving power of the first magnetic field resonator.

2. The apparatus of claim 1 further comprising a cylindrical cavity interior to the bodies of the first magnetic resonator and the second magnetic field resonator.

3. The apparatus of claim 1, wherein the first magnetic field resonator is an Alderman-Grant resonator and the second magnetic field resonator is a loop gap resonator.

4. The apparatus of claim 1, wherein the passive Q switch is configured to reduce the Q of the second magnetic field resonator in response to the driving power being above a threshold power level.

5. The apparatus of claim 4, wherein the passive Q switch is formed of a first pair of switching diodes and a second pair of switch diodes both pairs in parallel with the second magnetic field resonator to shortcut the second magnetic field resonator when the driving power is above the threshold power level.

6. The apparatus of claim 4, wherein the passive Q switch is formed of a first pair of switching diodes and a second pair of switch diodes both pairs in parallel with the second magnetic field resonator to shunt an excitation pulse power above a power threshold to a load coupled to the passive Q switch.

7. The apparatus of claim 1, wherein the first magnetic field resonator is a Electron paramagnetic resonance (EPR) or electron spin resonance (ESR) resonator and the second magnetic field resonator is an EPR or ESR resonator.

* * * * *

UNITED STATES PATENT AND TRADEMARK OFFICE
CERTIFICATE OF CORRECTION

PATENT NO. : 10,551,450 B2
APPLICATION NO. : 14/128423
DATED : February 4, 2020
INVENTOR(S) : Howard Halpern et al.

Page 1 of 1

It is certified that error appears in the above-identified patent and that said Letters Patent is hereby corrected as shown below:

In the Specification

At Column 1, Line 16:
"This invention was made with government support under Contract No. EB002034 awarded by the National Institute of Biomedical Imaging and Bioengineering of the U.S. Department of Health & Human Services and under Contract No. CA98575 awarded by the National Cancer Institute. The government has certain rights in the invention."

Should be:
""This invention was made with government support under grant numbers EB002034 and CA098575 awarded by the National Institutes of Health. The government has certain rights in the invention."

Signed and Sealed this
Twelfth Day of January, 2021

Andrei Iancu
*Director of the United States Patent and Trademark Office*